United States Patent [19]

Sato et al.

[11] Patent Number: 5,023,054
[45] Date of Patent: Jun. 11, 1991

[54] BLOOD FILTER AND APPARATUS FOR HEMORHEOLOGICAL MEASUREMENT

[75] Inventors: Kazuo Sato, Tokyo; Yuji Kikuchi, 108-402, Takezono-3-chome, Tsukuba-shi; Hiroshi Ohki, Tsuchiura; Toshio Kaneko, Katsuta, all of Japan

[73] Assignees: Hitachi Ltd., Tokyo; Yuji Kikuchi, Tsukuba, both of Japan

[21] Appl. No.: 433,897

[22] Filed: Nov. 9, 1989

[30] Foreign Application Priority Data

Nov. 11, 1988 [JP] Japan .................. 63-283687

[51] Int. Cl.$^5$ ............ G01N 11/00; G01N 15/00; G01N 21/00; G01N 27/00
[52] U.S. Cl. .................... 422/82.09; 422/73; 422/101; 422/82.01; 210/492; 210/483; 210/335; 377/11; 377/12; 324/71.4
[58] Field of Search ............ 422/73, 101, 82.01, 422/82.09; 210/492, 483, 335; 377/11, 12; 324/71.4

[56] References Cited

U.S. PATENT DOCUMENTS

| 2,982,416 | 5/1961 | Bell | 210/321 |
| 4,519,244 | 5/1985 | Meloy | 73/432 R |
| 4,778,657 | 10/1988 | Spohr | 422/73 |

FOREIGN PATENT DOCUMENTS

| 0094193 | 11/1983 | European Pat. Off. . |
| 0209711 | 1/1987 | European Pat. Off. . |
| 87/02265 | 4/1987 | World Int. Prop. O. . |

OTHER PUBLICATIONS

Gao, Shi-Jia et al., Nucleopore Filtration Test at Low Pressure for Clinical Application, National Cardiovascular Center and Institute of Hematology, Chinese Academy of Medical Science.

Ogura, Eiji et al., "Measurement of Red Blood Cell Deformability Using a Single Micropore on a Thin Si$_3$N$_4$ Film".

Ogura, E. et al., Parallel Measurement of Red Blood Cell Deformability through Micropore Array System on Si$_3$N$_4$ Membrane, Department of Electrical and Electronics Eng., Tokyo Inst. of Technology, 1989.

Abatti, Paulo Jose et al., "Development of a New Type of Micropipette and It's Application to Red Blood Cell Investigation", Technical Digest of the 8th Sensor Symposium, 1989, pp. 107-110.

Medical and Biological Engineering & Computing, vol. 21, No. 3, May, 1983, pp. 270-276, IFMBE, Stevenage, Herts, GB, Y. Kikuchi et al., "Improved Filtration Method for Red Cell Deformability Measure . . . ".

*Primary Examiner*—David L. Lacey
*Assistant Examiner*—David Redding
*Attorney, Agent, or Firm*—Antonelli, Terry, Stout & Kraus

[57] ABSTRACT

A filter and filtering apparatus for measuring the deformability of a blood cell passing through a flow passage formed as a space between a surface of a groove formed in a first substrate and a surface of a second substrate with which the groove is sealed. The filtering apparatus includes electrodes mounted at the inlets and outlets of the flow passages, or optical elements to enable cell deformity measurements.

12 Claims, 5 Drawing Sheets

BLOOD FILTER AND APPARATUS FOR HEMORHEOLOGICAL MEASUREMENT

BACKGROUND OF THE INVENTION

This invention relates to hemorheological measurement and, more particularly, to a blood filter, a method of and apparatus for hemorheological measurement Conventionally, membranes which have very small holes, e g., "Nuclepore" filters and nickel mesh filters are used to examine the filterability when blood passes through the filter, as described on pages 42 to 43 of the collection of papers prepared for the meeting of Nippon Biorheology Gakkai in 1988 (No. 7-31, 7-33 and 7-34). A "Nuclepore" filter is formed of a thin polycarbonate sheet with small holes formed therein, and a nickel mesh is formed of a thin nickel film with small holes formed therein. These types of filters are used in such a manner that blood is made to pass through the small holes by applying different pressures on the two sides of the filter membrane respectively, and that the time taken for the blood to pass through the filter is measured to estimate the filterability or the deformability of red blood cells.

Also, a method of using a filter constructed by forming small holes in an $Si_3N_4$ membrane formed on a surface of a silicon substrate to evaluate the deformability of red blood cells is known. An example of this method is described on pages 2,191 to 2,196 of the Denshi Jyoho Tsushin Gakkai Lecture Magazine D (1988).

In these conventional techniques, the sectional configuration of blood cells in the direction of passage through the filter cannot be observed although the existence of blood cells can be observed at the outlet or inlet of the filter.

Other problems are also encountered in that the length of the flow passages of the filter cannot be freely selected, that information on the size or volume of one blood cell cannot be separately obtained, and that blood cells passing through the holes of the filter are not uniformly deformed.

SUMMARY OF THE INVENTION

A first object of the present invention is to realize a uniform porous filter in which the diameter and the length of the filter holes can be set freely and in which the sizes of the flow passages are uniform.

A second object of the present invention is to enable the sectional configuration of each blood cell in the passing direction to be observed during passage through the flow passage of the filter.

A third object of the present invention is to have data on the size or volume of each blood cell separately from other data items.

A fourth object of the present invention is to reduce the dispersion of the evaluation of the deformability by uniformizing the process of deformation of blood cells passing through the flow passages of the filter.

To achieve these objects, in accordance with this invention, in place of membrane filters, a filter is constructed by sealing, with a flat plate, a surface in which fine grooves are formed to define a very fine flow passage through which the blood is passed.

To achieve, specifically, the first object, a micro machining technology for manufacture of semiconductors is utilized to form a multiplicity of uniform grooves in one substrate with improved accuracy. To achieve the second object, a plate having transparency is used as the flat plate for sealing the grooves. To achieve the third object, electrodes are disposed on a surface of the flat plate in such a manner that each pair of electrodes serve to detect an electric potential difference between the inlet and outlet of one groove. To achieve the fourth object, the sectional configuration of each groove is changed in the longitudinal direction thereof, thereby enabling a non-spherical blood cell to be positioned so as to face in a certain direction immediately before the blood cell enters a narrow portion of the groove of the filter.

The grooves to be formed in one substrate are formed by lithography and etching. Accordingly, the substrate can be formed with a multiplicity of grooves uniformly thereon with improved dimensional accuracy. Then the substrate and the flat plate are bonded together while being kept in contact with each other, thereby forming a filter free from the possibility of penetration of blood components through the connection interface and having flow passages uniform in size.

Blood cellular components, e.g., red blood cells flowing through the flow passages while being deformed can be observed via the flat plate with which the grooves are sealed.

The pair of electrodes are disposed at the inlet and the outlet of each flow passage to measure the size of each blood cell having an electric resistance different from that of plasma. That is, the electric resistance inside the flow passage varies in proportion to the volume of the blood cell occupying a certain capacity in the flow passage when the blood cell enters between the electrodes between which a certain voltage is applied, and the volume of the blood cell can be thereby calculated. The provision of the electrodes also makes it possible to obtain the time taken for each blood to pass through the flow passage, i.e., data on the deformability.

Guide portions are provided so as to make blood cells enter the filter section face in a certain direction preliminarily, thereby uniformizing the processes of deformation of blood cells passing through the flow passages of the filter.

DESCRIPTION OF THE PREFERRED EMBODIMENTS

Figure 1:
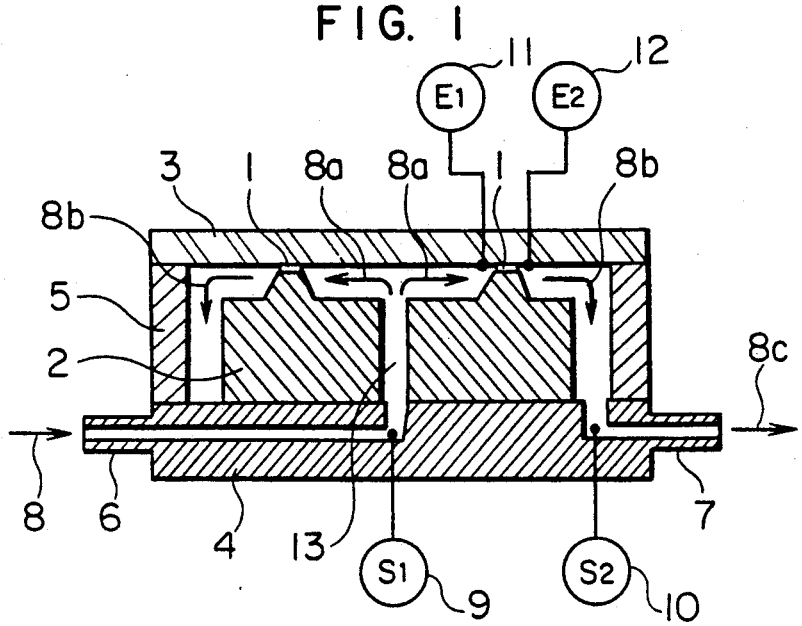
FIG. 1 is a cross-sectional view of a blood filter in accordance with an embodiment of the present invention.

An embodiment of the present invention will be described below with reference to FIG. 1. FIG. 1 shows a cross-sectional view of a blood filter in accordance with the present invention. Small holes 1 which serve as flow passages through which blood components can be passed are formed by a single crystal silicon substrate 2 and a flat glass plate 3. A base plate 4 and an outer tube 5 are provided to enable blood to be introduced into the small holes 1 and thereafter discharged. The base plate 4 is provided with an inlet 6 for introducing blood and an outlet 7 for discharging the blood 7. Blood can flow as indicated by arrows 8, 8a, 8b and 8c shown in FIG. 1. Pressure sensors 9 and 10 are provided to monitor pressures inside the flow passages, i.e., to detect the difference between the pressures on the upstream and downstream sides of the small holes 1 in order to constantly maintain this pressure difference. Pairs of electrode plates 11 and 12 are formed by patterning on the flat glass plate 3 in the vicinity of the inlets and outlets of the small holes and are led to the outside. The electrode plates 11 and 12 are used to detect whether or not any blood cells pass through the small holes, the size of the blood cells, and the time required for the passage of the blood cells Referring then to FIG. 2A, details of the single crystal silicon substrate 2 for forming the small holes are illustrated. A through hole 13 for introducing blood is formed in the substrate at the center thereof, and a bank 14 which constitutes a filter is formed around the through hole 13. As can be clearly seen in an enlarged vertical cross-sectional view of one section of the bank 14 (refer to FIG. 2B), bank 14 has a flat upper surface for connection to the flat glass plate, and a multiplicity of microscopic grooves 15 through which blood cells can be passed are formed in the upper surface of the bank 14. Some of the cellular components of blood introduced through the blood inlet, e.g., red blood cells in the flows of plasma pass through the groove sealed with the glass plate with those components being deformed.

A process of manufacturing the main filter portion will be described below. The single crystal silicon substrate is formed from a wafer having a crystallographic 100 orientation and a thickness of about 1 mm. A filter for measuring the deformability of red blood cells having a diameter of about 8 $\mu$m is formed by, for example, in the following manner. A bank having a width of 10 $\mu$m is formed into a regular square having a size of about 10×10 mm within a region of a silicon chip which is generally 15 mm square. In a first step of the process, about 700 parallel grooves having a width of 6 $\mu$m and a depth of 6 $\mu$m are formed by etching so as to be perpendicular to each of the four sides of the square. The pitch of the arrangement of the grooves is about 15 $\mu$m, the positions of the grooves correspond to the portion from which the bank is thereafter formed, and the length of the grooves is long enough to cover the width of the bank. Thereafter, portions of the wafer defined inside and outside the bank are deeply etched to form the bank. The height of the resulting bank is about 100 $\mu$m. In this process, it is important to exactly adjust one side of the bank extending along the square line to the 110 direction of the crystal. In this step, the whole surface of the wafer including the inner groove surfaces is first covered with a layer of $SiO_2$ or $Si_3N_4$, and the $SiO_2$ or $Si_3N_4$ surface layer is then removed except for the region corresponding to the bank, i.e., strip-like portions about 10 mm square having a width of 10 $\mu$m to form an etching mask. A hot lithography technique is used for this step. The silicon substrate is thereafter etched by using an anisotropic etching liquid such as a KOH water solution, thereby effecting etching until the etched recess has a depth of about 100 $\mu$m with the width of the upper surface of the bank being maintained with accuracy, as shown in FIG. 2B. As a result, surfaces 15a remain as slanting surfaces of the bank.

After etching, the remaining $SiO_2$ or $Si_3N_4$ surface layer is removed from the surface of the silicon substrate, and a plate having a thickness of about 1 mm and formed of a Pyrex glass is placed on and connected to the upper surface of the substrate, thereby completing the small holes. For the connection between glass and silicon, it is preferable to utilize a method of anodic bonding in which a DC voltage of several hundred volts is applied to the bonded interface in an atmosphere of a temperature of about 400° C. This method eliminates the risk of leakage of the specimen through the interface between glass and silicon. However, according to use, a method of mechanically retaining the glass and the silicon substrate in a super posed state can be adopted in consideration of convenience of cleaning during repeated use of the filter.

As is apparent from this working process, the size of the grooves formed in the single crystal silicon by working based on lithography and etching can be selected as desired, and the uniformity of the sizes of the grooves is high even if the number of the grooves is large, thus achieving the first object of the present invention. Also, the second object of the present invention relating to visualization of the deformation of blood cells during passage through the filter can be achieved by observation from the surface of the "Pyrex" glass.

Figure 3:
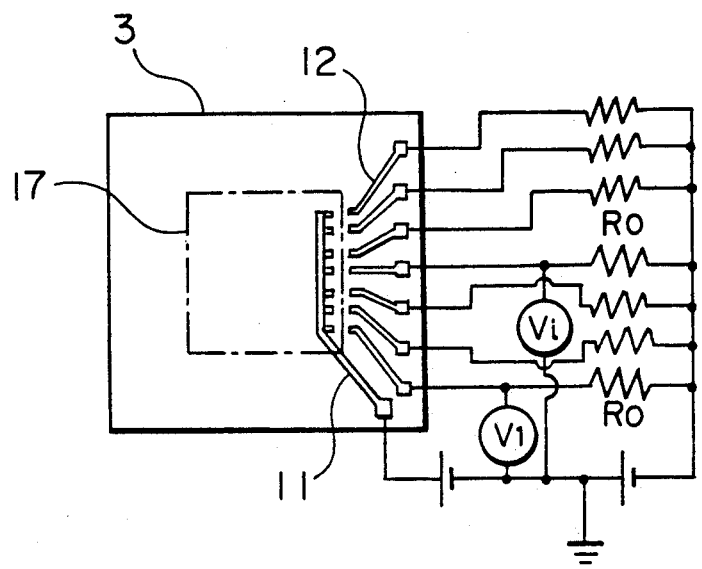
FIG. 3 is a front view of a flat glass plate on which electrodes are disposed.
Figure 4A:
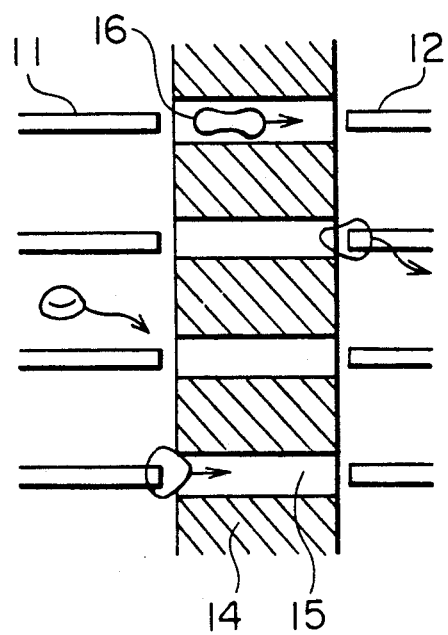
FIG. 4A is a diagram of the arrangement of the electrodes on the upstream and downstream sides of small holes of the filter.

Next, functions of acquiring data on the volume of blood cells relating to the third object of the present invention will be described below. For this purpose, the pairs of electrodes 11 and 12 are disposed on the upstream and downstream sides of the filter, as shown in FIG. 1. FIGS. 3 and 4 show a method of placing the electrodes and the principle of blood cell volume measurement. FIG. 3 shows the upper surface of the flat glass plate 3, the chain line in FIG. 3 indicates the position of the bank extending along the square line. Inside the bank are disposed the common electrodes 11 formed by patterning in positions corresponding to the small holes. The electrodes 12 opposed to the electrodes 11 are disposed in association with the respective small holes and are independently led to the outside. FIG. 4A shows an enlarged view showing the relationship between the small holes and the electrodes. The electrodes 11 and 12 are formed by depositing, for patterning, platinum on the flat glass plate and are fixed after being correctly positioned at the inlets and outlets of the grooves 15 on the bank 14.

The volume of blood cells can be measured by using these electrodes on the basis of the following principle. If the electric resistance of a blood cell is $r_x$, the volume of the blood cell is x, the total volume in the small hole is v, and further the resistivity of plasma is r, the resistance R between the electrodes 11 and 12 when the blood cell exists in the small hole can be expressed by the following equation $$R = \left\{1 + \left(\frac{r_x}{r} - 1\right) \cdot \frac{r}{v}\right\} R_0 \quad (1)$$

where $R_0$ represents a resistance when no blood cell exists in the small hole. $R_0$ is expressed by an equation with a sectional area a and a length l:

$$R_0 = r\frac{l}{a} \quad (2)$$

The volume x of the blood cell can be calculated as a function of the resistance between the electrodes by utilizing the relationship expressed by equation (1). There are conditions of the calculation of the volume using equation (1) that the volume x of the blood cell is smaller than the volume of the small hole, and that the diameter of the blood cell is larger than the diameter of the small hole.

Figure 4B:
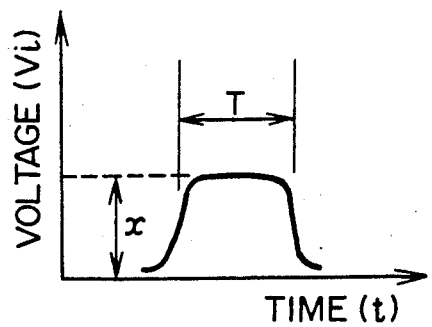
FIG. 4B is a graph showing an example of the signal obtained by the electrodes.

FIG. 3 also shows an example of a circuit for obtaining the change in the resistance between the electrodes as a voltage signal. A voltage signal Vi which represents a result of detection that a blood cell has entered the i-th small hole changes with time, as shown in the graph of FIG. 4B. Data on the volume of the blood cell is obtained from a height X of the waveform while the time required for the passage of the blood cell is obtained from the width of the waveform. The third object of the present invention is achieved by this method.

Figure 5:
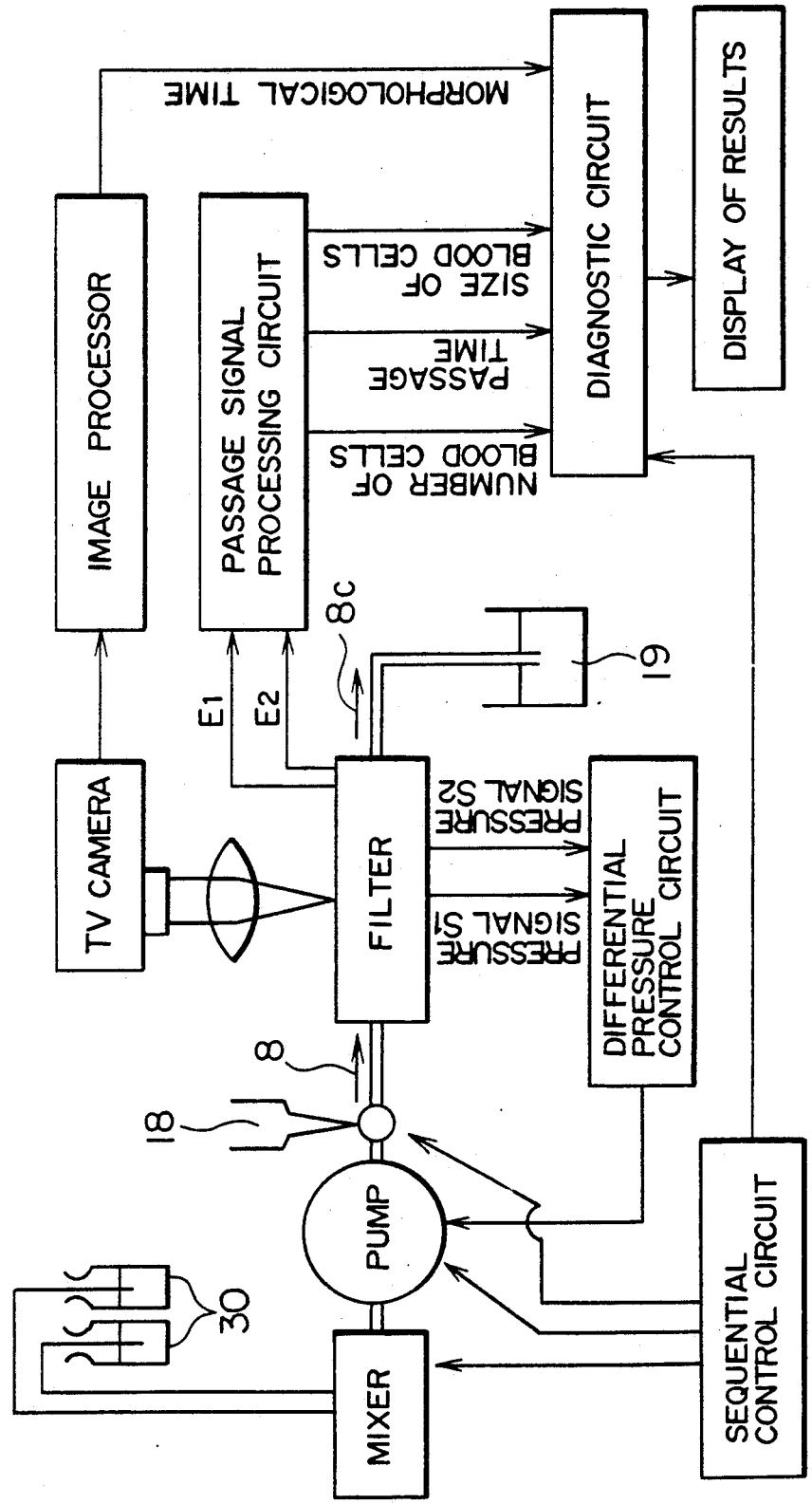
FIG. 5 is a diagram of the construction of an example of a hemorheological measurement apparatus in accordance with the present invention.

FIG. 5 shows an example of a hemorheological measurement apparatus based on the combination of the above-described means. This apparatus operates to introduce blood injected through a sample inlet 18 into a discharge section 19 via the filter in accordance with the present invention. The apparatus is not only capable of directly introducing the blood into the filter but also capable of mixing the blood in a different liquid such as a physiological saline or a liquid containing a physiologically active substance and thereafter introducing the mixture into the filter. For this operation, a plurality of solution bottles 30 are connected to the flow passage through a mixer. The difference between the pressures on the upstream and downstream sides of the filter is controlled by a circuit for differential pressure control so as to be maintained at a predetermined pressure. Morphological data on blood cells is obtained by observation with a TV camera through the glass of the filter, and information on whether or not any lesion exists is extracted by an image processor. Data on the number of blood cells, the time required for the passage, the size of blood cells is obtained from the change in the resistance between electrodes $E_1$ and $E_2$ by a signal processing circuit. A diagnostic circuit combines these information items to obtain the result of diagnosis.

An example of algorism for diagnosis will be described below.

The volume and the passage time of individual blood cells can be detected, and the numbers of blood cells having passage time and the volume in particular ranges are expressed by a histogram. Accordingly, by obtaining the result of the measurements about a lot of blood cells, it is possible to prepare such frequency histogram in two variable parameters as shown in FIG. 6.

Whether the sample blood is normal or not can be judged statistically by comparing a histogram 21 relating to normal blood and a histogram 22 relating to a sample blood.

For example, changes in red blood cell deformability can be detected by this method even when their effects on passage time are masked by change in cell volume.

Figure 6:
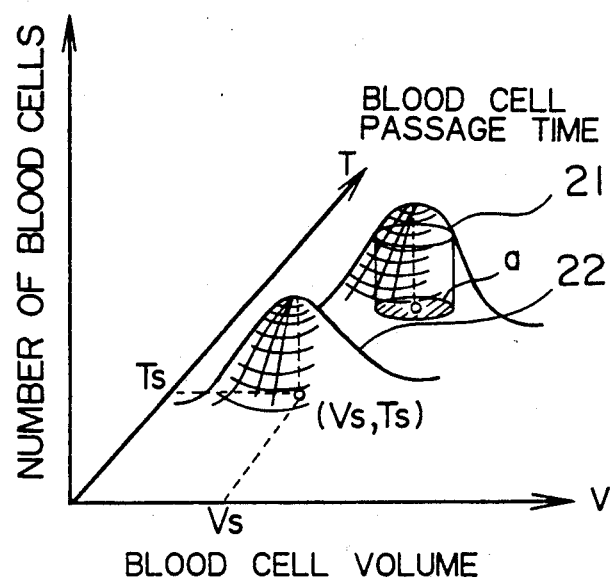
FIG. 6 is a three-dimensional display graph showing the concept of a histogram used for a diagnosis algorism.

More concretely, it is the simplest method to compare a permissible range of deviation (a) in the histogram 21 relating to a normal blood (illustrated by hatching) and a value (Vs, Ts) if the volume of blood cell and the passage time of blood cell which correspond to the peak in the histogram 22 relating to the sample blood are respectively Vs and Ts on the coordinate which consists of axes of the volume of blood cell and the passage time of blood cell in FIG. 6.

That is, it is possible to judge whether or not a significant difference between the normal blood and the sample blood exists by detecting whether or not a value of maximum likelihood (Vs, Ts) is within the range (a). It is possible to further improve the reliability of the diagnosis by a statistic analysis which effects numerical processing in a similar manner with respect to the correlation between three or more information items, for example, the existance of hemolysis, the viscosity of blood and the reaction of physiologically active substances.

For health examination, data on whether or not a hemolysis, i.e., rupture of erythrocytes takes place is important. Whether or not blood cells rupture during the passage through the blood filter can be known by observation with the TV camera through the filter section and can be also detected as a change in the color of the plasma in such a manner that, as shown in FIG. 5, a sample 8c flowing out of the filter to the discharge section 19 is introduced into a transparent pipe, and the absorbancy of the sample is measured by transmitting light through the sample. This is particularly useful when changes in several quantities take place simultaneously and their effects on passage time counteract each other.

Further, the viscosity of blood can be measured by selecting a size of the holes of the blood filter larger than the diameter of blood cells. Let the viscosity of blood be $\mu$, the representative size (diameter) of the filter hole be d, the length be L, the difference between the pressures on the upstream and downstream sides of the filter be $\Delta P$, and the flow rate be Q. Then, a relationship:

$$\mu \propto \frac{d^4 \Delta P}{Q \cdot L}$$

is established from the equation of Hagen-Poiseuille. An abnormality of the coefficient of viscosity can be found from this relationship.

To put the present invention into practice, it is effective to provide the surfaces of the small holes of the filter with hydrophilic properties. For this purpose, it is desirable to cover the silicon surface with a silicon dioxide film. Further, the blood cell transit velocity can be greatly changed by coating the surfaces of the small holes with a material interactive with blood cells. It is thereby possible to selectively extract characteristics of blood cells. For this purpose, it is effective to previously coat the small hole surfaces with a specific polymer material such as a protein.

The velocity at which blood cells pass through the filter can also be greatly changed by mixing a physiologically active substance in the sample blood. This effect can be achieved in the case of the hemorheological measurement apparatus shown in FIG. 5 by providing a passage for mixing, through the mixer, a physiologically active substance in the sample flow before it enters the filter. For example, if a physiologically active substance FMLP acts on white blood cells, the velocity at which white blood cells pass through the filter is greatly reduced. Platelets coagulate by the effect of addition of ADP, resulting in a deterioration of the filterability of the blood. It is possible to separate blood data items including that on the activity of white blood cells and that on the coagulability of platelets by utilizing such selective changes in the activity. Various types of sensors may be disposed in the flow passage from the blood inlet 18 to the outlet 19 to simultaneously detect the osmotic pressure, the ion concentration, and so on, thereby achieving more precise analysis.

Figure 2A:
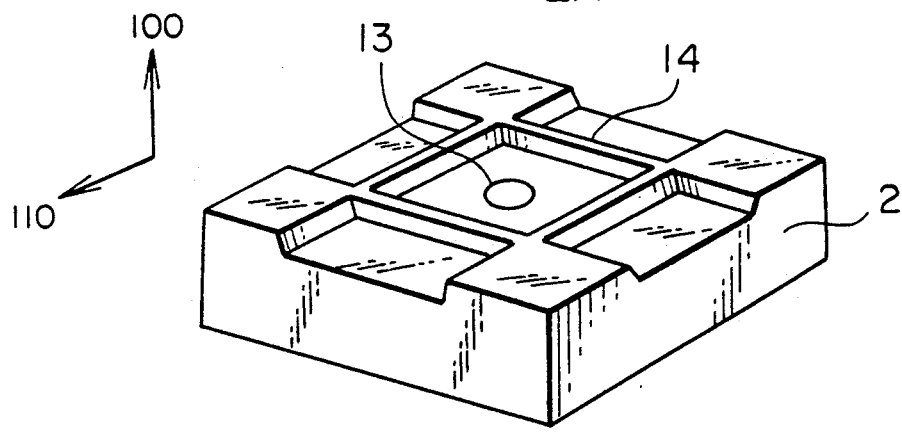
FIG. 2A is a diagram of a blood filter.
Figure 2B:
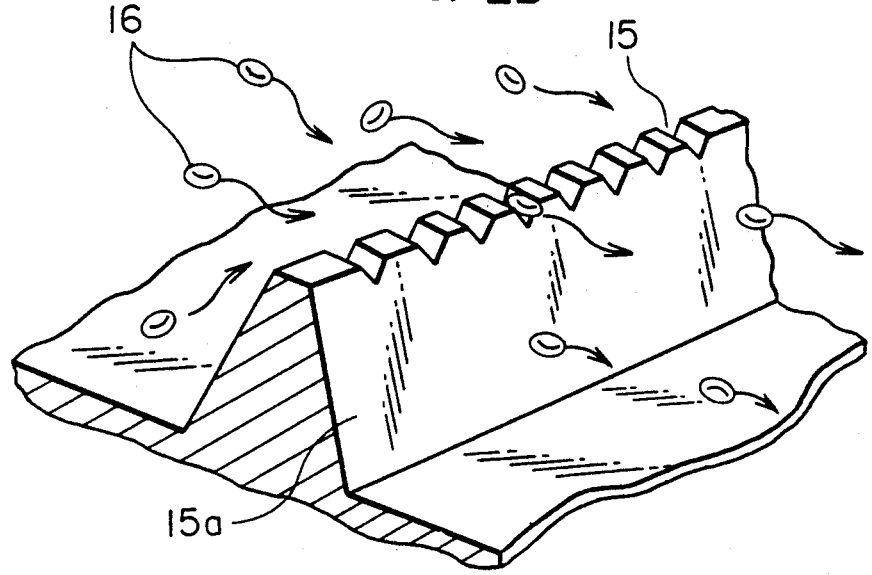
FIG. 2B is an enlarged diagram of a bank shown in FIG. 2A.
Figure 7:
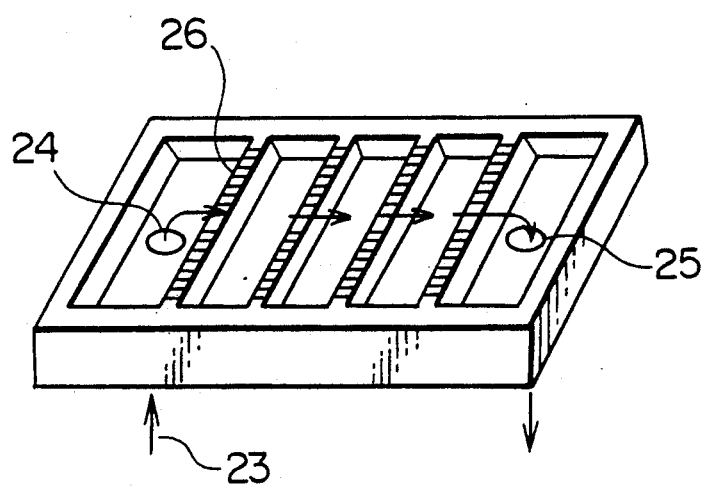
FIG. 7 is a schematic diagram showing the appearance of a silicon chip used for blood chromatograph.

The blood filter shown in FIG. 2A is a single-stage filter. However, a chromatograph can be made if the blood filter is constructed as a cascade type. A cascade filter can be constructed on one silicon chip, as shown in FIG. 7. That is, four stage-bank portions 26 are formed between a blood inlet 24 and a blood outlet 25. Because the time required for the passage through one stage-filter stage varies depending upon the deformability, blood cells passed through the cascade filter are classified with respect to the degrees of deformability on the basis of the time taken to reach the outlet. Blood cells classified may be extracted for examination of their other characteristics.

Figure 8:
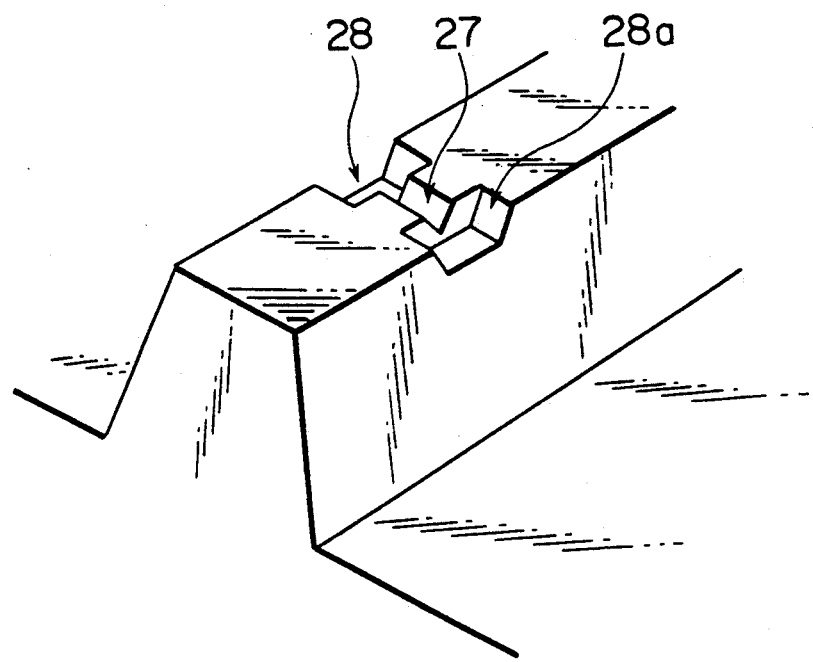
FIG. 8 is a schematic enlarged diagram of a portion of a blood filter chip in accordance with another embodiment of the present invention.

In the described embodiment, the structure of the filter is uniform in the longitudinal direction. However, other types of structure may be adopted. For example, as shown in FIG. 8, if the silicon substrate is worked so as to change the sectional configuration of each groove changed in the longitudinal direction and then sealed at the upper surface with a flat glass plate, the following effects can be achieved.

First, the orientation of each blood cell moving toward a filter section 27 can be set to a certain direction in a guide portion 28 positioned on the upstream side. It is thereby possible to uniformize, in particular, the processes of deformation of non-spherical blood cells in the filter section. As a result, the dispersion of data on the deformability of blood cells is reduced and the reliability of the information is improved.

Figure 9:
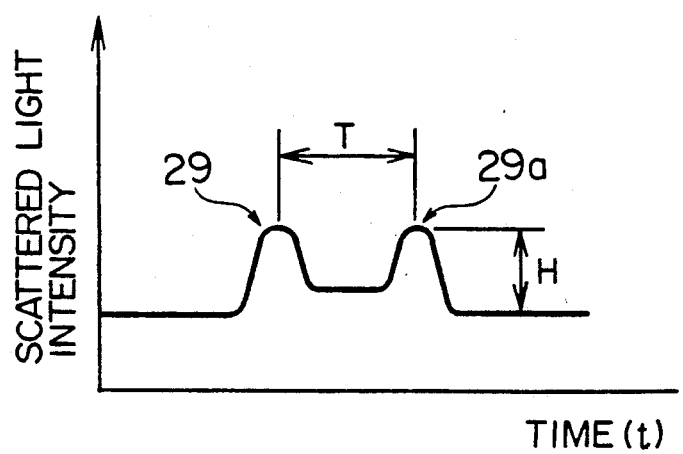
FIG. 9 is a graph showing changes in the reflected light intensity with time when the passage of a blood cell is detected by using light.

A second effect resides in that the volume of each blood cell and the filter passage time can be measured by an optical means without using the above-described electrode structure. In this case, the structure of the filter is such that grooves 28 and 28a having a size generally equal to or slightly larger than the diameter of the blood cell are formed on the upstream and downstream sides of a filter section 27, as shown in FIG. 8. The surfaces of the above constructed grooves are irradiated with a light beam to measure the reflected light intensity during the passage of the blood cell. FIG. 9 shows a result of a measurement using this filter structure. Peaks 29 and 29a of the waveform correspond to scattered light produced when the blood cell passes through the grooves 28 and 28a, and the height H of the peaks is used as data on the volume of the blood cell. The time interval T between the two peaks corresponds to the time taken for the blood cell to pass through the filter.

This embodiment can be realized by providing a light source, a lens system and an optical system instead of conducting image processing with a TV camera. It is therefore possible to construct a low-cost system.

In a measurement system for detecting passage of a blood cell from changes in the resistance between the electrodes or from changes in the scattered light intensity, an unusable state by clogging of blood cells in the filter can be known from an abnormal value of the resistance between the electrodes or from an abnormal value of the reflected light intensity. A hemorheological measurement system can be easily constructed to alarm the operator for exchange of the filter from an abnormal signal representing such an abnormality. To reduce the frequency of exchange of the filter by obstructions therein, the arrangement may be such that a plurality of filter systems are formed on one silicon chip and each filter system is selected by suitably changing over flow circuits, thereby achieving a further improvement in the efficiency of hemorheological measurement.

What is claimed is:

1. A blood filter comprising a first substrate having a plurality of small grooves formed on a surface thereon; a second substrate having a flat surface abutting on portions of the surface of the first substrate located between said grooves on said surface of said first substrate to form a plurality of blood flow passages constructed so as to filter blood between the first and second substrates, each of said blood flow passages having an inlet end and an outlet end; and inlet means for introducing blood into the inlet ends of said blood flow passages and outlet means for discharging blood received from the outlet ends of said blood flow passages.

2. A blood filter according to claim 1, wherein said first substrate is formed of a single crystal silicon.

3. A blood filter according to claim 1, wherein said second substrate is transparent.

4. A blood filter according to any one of claims 1 to 3, further comprising a pair of electrodes disposed in the vicinity of the inlet end and the outlet end of one of said blood passages.

5. A blood filter according to claim 1, wherein said blood filter comprises a plurality of serially arranged said passages forming a cascade arranged filter apparatus.

6. A blood filter according to claim 1, wherein a cross-sectional configuration of each of said blood flow passages is formed so as to change in a direction in which the blood flows therethrough.

7. A blood filter according to claim 1, wherein a hydrophilic coat is formed on a surface of each of said blood flow passages.

8. A blood filter according to claim 1, wherein each surface of said blood flow passages is coated with a polymer material.

9. A blood filter according to any one of claims 1, 2, 3, 5, 6, 7 and 8, further comprising means for creating a pressure difference of the blood between said inlet means and said outlet means and means for providing a signal representing the number of blood cells passing through said filter, the passing time, and/or the size of the blood cells.

10. An apparatus for hemorheological measurement according to claim 9, further comprising means for irradiating the blood flowing through each of said blood flow passages of said blood filter, and means for detecting scattered light from blood cells in the blood.

11. An analyzer comprising said blood filter according to claim 9, further comprising means for measuring the difference between the times taken for blood cells of the blood to pass through said blood filter.

12. A blood filter comprising a first substrate including a surface having a plurality of grooves formed thereon; a second substrate contacting the first substrate so as to form a plurality of blood flow passages within said grooves through which blood is permitted to flow; means for causing blood to flow through blood flow passages, and said second substrate including transparent means for observing the blood flowing in said flow passages from a surface of said second substrate.

* * * * *